(12) United States Patent
Quetel et al.

(10) Patent No.: US 8,470,240 B2
(45) Date of Patent: Jun. 25, 2013

(54) METHOD AND DEVICE FOR STERILIZING PREFORMS

(75) Inventors: François Quetel, Octeville sur Mer (FR); Stéphane Hebert, Octeville sur Mer (FR)

(73) Assignee: Sidel Participations, Octeville sur Mer (FR)

( * ) Notice: Subject to any disclaimer, the term of this patent is extended or adjusted under 35 U.S.C. 154(b) by 885 days.

(21) Appl. No.: 11/959,814

(22) Filed: Dec. 19, 2007

(65) Prior Publication Data

US 2008/0152538 A1      Jun. 26, 2008

(30) Foreign Application Priority Data

Dec. 20, 2006   (FR) ...................................... 06 11145

(51) Int. Cl.
*A61L 2/00*   (2006.01)
*B01J 19/00*   (2006.01)

(52) U.S. Cl.
USPC .............................. 422/28; 422/291; 422/292

(58) Field of Classification Search
USPC .......................................... 422/291, 292, 28
See application file for complete search history.

(56) References Cited

U.S. PATENT DOCUMENTS

| | | | |
|---|---|---|---|
| 5,879,648 A * | 3/1999 | Hada et al. ..................... | 422/304 |
| 6,183,691 B1 | 2/2001 | Swank et al. | |
| 6,537,492 B1 * | 3/2003 | Sogaard .......................... | 422/21 |
| 6,562,281 B1 * | 5/2003 | Marchau et al. ............... | 264/532 |
| 6,984,360 B1 * | 1/2006 | Feuilloley et al. .............. | 422/28 |
| 7,284,778 B1 | 10/2007 | Pellegatta | |
| 2001/0010145 A1 | 8/2001 | Tawa et al. | |
| 2002/0159915 A1 * | 10/2002 | Zelina et al. ...................... | 422/3 |
| 2004/0191114 A1 | 9/2004 | Frost et al. | |

FOREIGN PATENT DOCUMENTS

| | | |
|---|---|---|
| AU | 763393 B2 | 9/2000 |
| EP | 0 243 003 A2 | 10/1987 |
| FR | 2 766 121 A1 | 1/1999 |
| FR | 2 774 912 A1 | 8/1999 |
| FR | 2 789 932 A1 | 8/2000 |
| JP | 10-119934 A | 5/1998 |
| JP | 2001-212874 A | 8/2001 |
| WO | 99/03667 A1 | 7/1998 |

\* cited by examiner

*Primary Examiner* — Kevin Joyner
(74) *Attorney, Agent, or Firm* — Sughrue Mion, PLLC

(57) ABSTRACT

The method includes at least the following steps of spraying a flow of sterilizing vapor, including a vaporized sterilizing product, towards the preforms to be sterilized, so as to cover at least an inner wall (15) of the preforms to be sterilized with the product; and heating, by radiation, the preforms covered with sterilizing product in order to bring them to a temperature (T2) at or above an activation temperature (Ta) for the product. The spraying of the flow of sterilizing vapor is carried out in a protective chamber (40), heating is carried out outside the protective chamber (40), and the flow of sterilizing vapor is in the form of a jet of vapor (F) vaporized onto the preforms (12), in such a way as to bring about the deposition, by condensation, of a substantially uniform film of condensate (48) of sterilizing product on at least the inner wall (15) of the preforms to be sterilized.

18 Claims, 2 Drawing Sheets

METHOD AND DEVICE FOR STERILIZING PREFORMS

The invention concerns a method and a device for sterilizing preforms.

The invention concerns more particularly a method for sterilizing a preform of plastics material intended to be moulded, especially by blow moulding.

The document WO 99/03667 A1 describes a plant for producing sterile bottles starting from preforms of plastics material, of the type in which the preforms are conveyed inside the plant in a continuous stream which circulates from upstream to downstream. The plant carries out the method which consists in:

moistening the preform upstream of the heating means,
   transferring the preform to the heating means,
   heating the moistened preform by radiation to sterilize it.

This type of plant has the drawback of requiring a high flow rate of sterilizing product and/or injection pressure for the sterilizing product in order to succeed in entirely covering the inner walls of the preforms so as to completely sterilize the inside of the preforms.

As a consequence, the sterilizing product consumption of the plant is high and the sterilizing operation is expensive.

In addition, the use of a high flow rate of sterilizing product may lead to the deposition of (residual) droplets of sterilizing product of large size on the inner walls of the preforms. During the heating of the preforms, these droplets produce a magnifying glass effect on the thermal radiation of the heating, leading to the appearance of spots on the walls of the bottles produced from the preforms in question.

In fact, in the plants of the prior art, the sterilizing product is sprayed in the form of a heavy condensate and at a pressure obtained by compressing, at pressures of around 2 to 3 bar, a gas, such as compressed air, which is sterilized and heated, for example at a temperature of the order of 130° C., so as to activate the sterilizing product thermally.

It is for this reason that the droplets of sterilizing product form an excess which is not completely vaporized during heating, such that each droplet produces a magnifying glass effect on the material of the preform, generally made of polyethylene terephthalate (PET), by the sterilizing product.

This phenomenon leads to the appearance of spots on the walls of the bottles, this defect in the appearance still sometimes being termed "orange peel" effect.

Moreover, the walls of the preforms are not uniformly covered by the droplets of sterilizing product, such that unsterilized areas remain between each of the droplets, on the surface of the inner and/or outer walls of the preform.

In addition, depending on the profile of the inner wall of each preform, it is not always possible to be certain of reaching to the bottom of the preforms, even with a high level of flow rate and/or pressure, by reason of the creation of a plug of over-pressure at the bottom of the preforms.

It is therefore an aim of the present invention to remedy these drawbacks and to propose, in particular, a sterilizing method and device which does not lead to the appearance of droplets, while reducing the consumption of sterilizing product.

To this end, the invention proposes a method for sterilizing a line of preforms made of plastics material that are intended to be moulded, especially by blow moulding, including at least the following steps:

spraying a flow of sterilizing vapour, including a vaporized sterilizing product, towards the preforms to be sterilized, so as to cover at least an inner wall of the preforms to be sterilized with the product, and heating, by radiation, the preforms covered with sterilizing product in order to bring them to a temperature at or above an activation temperature for the product, the method being characterized in that
   the spraying of the flow of sterilizing vapour is carried out in a protective chamber,
   heating is carried out outside the protective chamber, and
   the flow of sterilizing vapour is in the form of a jet of vapour vaporized onto the preforms, in such a way as to bring about the deposition, by condensation, of a substantially uniform film of sterilizing product condensate on at least the inner wall of the preforms to be sterilized.

According to other features of the method:
   the jet of vapour extends in a curtain, and the preforms file through this curtain;
   the method includes a step of extraction of the atmosphere from the protective chamber;
   extraction is carried out at an extraction rate low enough for the flow of sterilizing product not to be noticeably deflected;
   the protective chamber is pierced only by entry/exit openings for the preform and by an extraction opening;
   the rate of extraction through the extraction opening is regulated to be equal to the sum, on the one hand, of an escape flow rate penetrating through the entry/exit openings and, on the other hand, of the flow rate of the flow of sterilizing vapour less 15% to 20% of the flow rate of sterilizing product sprayed in the flow of sterilizing vapour; and
   the temperature to which the preforms are brought is substantially equal to a temperature for moulding the preforms by blow moulding and which is respectively above the activation temperature and an evaporation temperature of the sterilizing product.

The invention also has as its subject a device for sterilizing a line of preforms made of plastics material that are intended to be moulded, especially by blow moulding, comprising:

a spraying station including at least one nozzle for spraying a flow of sterilizing vapour, including a vaporized sterilizing product, towards the preforms to be sterilized, in such a way as to cover at least an inner wall of the preforms to be sterilized with the product, a heat conditioning station including a radiation oven intended to bring the preforms to a temperature at or above an activation temperature for the sterilizing product, in such a way as to sterilize at least the inner wall of the preforms, means for transporting the preforms to the spraying station, then to the heat conditioning station, characterized in that:
   the spraying station further includes a protective chamber in which each nozzle is located,
   the heat conditioning station is located outside the protective chamber, and
   at the spraying station, the flow of sterilizing vapour is vaporized in the form of a jet of vapour vaporized onto the preforms in such a way as to bring about the deposition, by condensation, of a substantially uniform film of sterilizing product condensate on at least the inner wall of the preforms to be sterilized.

According to other features of the device:
   the spraying station includes extraction means for extracting the atmosphere from the protective chamber;
   the extraction means are regulated in such a way that the extraction rate is low enough for the flow of sterilizing product not to be noticeably deflected;
   each nozzle has a mean axis of spraying of the sterilizing vapour towards the neck, the mean axis of spraying being on the one hand generally parallel to the axis of the transported preforms, and on the other hand radially eccentric relative to the axis of the preforms; and the transport means include at least one means, such as an inner core, which penetrates axially inside the neck of each preform, obstructing all or part of the inner opening defined by the neck, so as to increase the degree of sterilization by increasing the length of time for which the inner wall of the preform is exposed to the sterilizing product.

Other features and advantages of the invention will become clear from the following detailed description, for understanding of which, reference will be made to the appended drawings, in which.

In the continuation of the description, similar or identical elements will be designated by the same references.

Figure 1:
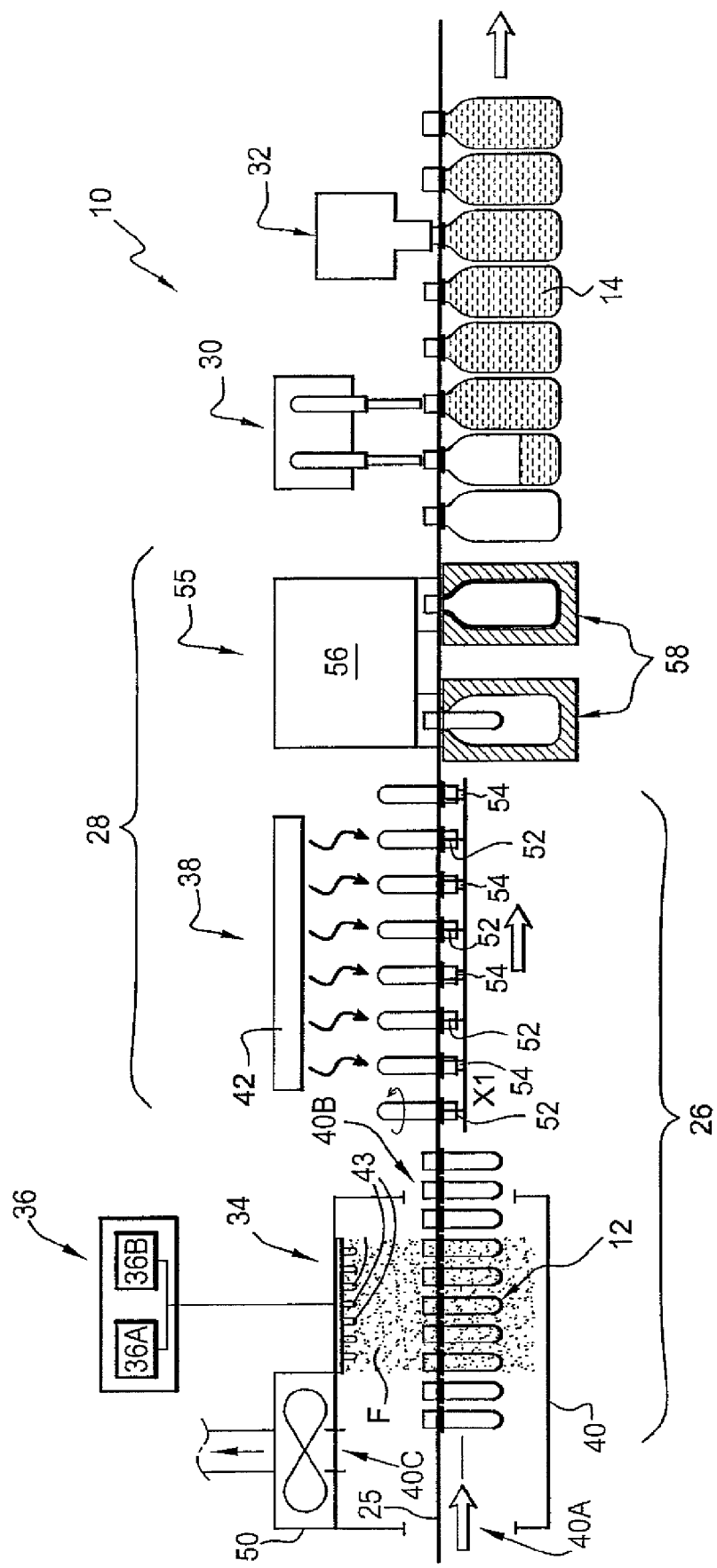
FIG. 1 is a diagram which represents an exemplary embodiment of a plant producing sterile bottles by blow moulding and including a sterilizing unit implementing the sterilizing method according to the invention.

FIG. 1 shows a plant 10 producing containers such as bottles 14, in particular sterile or asepticized bottles, which are advantageously obtained by blow moulding, starting from preforms 12 made of plastics material, for example of polyethylene terephthalate (PET).

Each preform 12 is in the general shape of a tube of U-shaped longitudinal section which is closed at one end and the other end of which already has the final shape of the neck 16 of the bottle 14.

Figure 2:
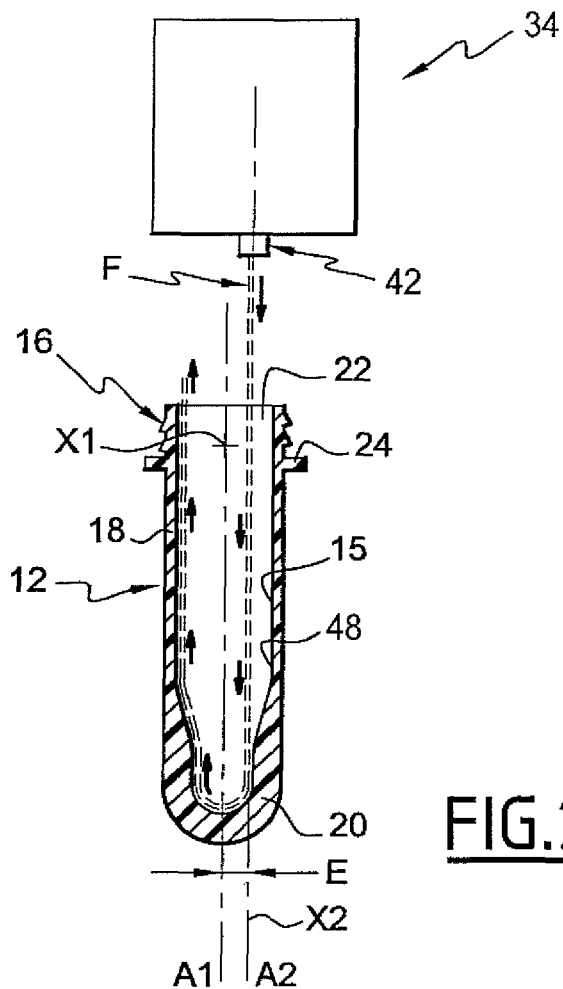
FIG. 2 is a view in axial section along the section plane II-II in FIG. 3, which shows diagrammatically a preform in the sterilizing unit of the plant of FIG. 1.

In FIG. 2, a preform 12 is shown, by way of non-limiting example, with the axis A1 of its cylindrical body 18 which extends vertically and which coincides with the axis of the neck 16.

The lower end 20 of the preform 12 is closed, in the general shape of a hemisphere, while its upper end forms the neck 16, which defines an inner opening 22 and which is in this case provided with an outer radial collar 24.

The preforms 12 are generally produced according to an injection-moulding process and moulded at a site other than that at which the plant 10 is located.

For certain applications, the bottles 14 obtained from the preforms 12 must exhibit a certain degree of sterility. For this reason an operation of sterilization of the preforms 12 is carried out in the plant 10 for the production of the bottles 14.

More precisely, the sterilization operation concerns as a priority the neck 16 and the inner wall 15 of the preform 12 corresponding to the inner wall which defines the internal volume of the bottle 14 intended to be filled.

With reference to FIG. 1, the plant 10 comprises means for transporting the preforms, in the form of a conveyor rail 25. Thus, the preforms 12 are conveyed within the plant 10 in a continuous stream which circulates from upstream to downstream, i.e. from the left to the right in FIG. 1.

The plant 10 includes, from upstream to downstream, on the one hand a sterilizing unit 26 for sterilizing the preforms 12 and, on the other hand, a forming unit 28 for the sterilized preforms 12 to form the bottles 14.

Advantageously, the plant 10 also includes, following the forming unit 28, a filling unit 30 and a stoppering unit 32. These two latter units are well known and will not be described in more detail.

The sterilizing unit 26 includes a spraying station 34 for spraying sterilizing vapour, fed with sterilizing vapour by sterilizing vapour preparation means 36. The sterilizing unit 26 also includes a heating station 38.

The sterilizing vapour preparation means 36 include heating means 36A for heating a sterilizing product in order to vaporise it, and a source of air 36B, advantageously compressed and/or sterilized by any suitable means, which is arranged for spraying the vaporized sterilizing product through the nozzles described hereinafter. The mixture of vaporized sterilizing product and air forms the flow of sterilizing vapour.

Preferably, the compressed air is dehydrated and circulates at a low speed in a directional flow so as to constitute a vector for the vaporized sterilizing product.

Preferably, the sterilizing product consists of a compound containing hydrogen peroxide or of vaporized hydrogen peroxide ($H_2O_2$) which, at the spraying station 34, is sprayed towards the preforms 12 in the form of a jet of gas including sterilizing product in the vapour state, advantageously a jet of dry vapour.

For example, the sterilizing product is a mixture of 25% of $H_2O_2$ in 75% of water.

The sterilizing vapour thus consists on the one hand of the vaporized sterilizing product, and on the other hand of hot air.

Preferably, the proportion P (by volume) of vaporized sterilizing product in relation to the hot air is between 10% and 15%. The proportion of hot air is therefore 100%-P.

The spraying station 34 further comprises a protective chamber 40 for protection against the diffusion of vapours.

The protection is intended first of all for the machine operators, since the sterilizing product vapours are generally harmful to health. The protection is also intended for the other elements of the plant 10, especially the heating station 38, which could be degraded by the corrosive effect of the sterilizing product.

The protective chamber 40 is hermetically sealed, except for openings for the entry 40A and exit 40B of the preforms 12, and an upper extraction opening 40C for the vapours. The entry/exit openings 40A, 40B for the preforms are preferably configured just to allow free passage to the preforms 12. Removable shields (not shown) are provided to close off portions of the openings 40A, 40B when the preforms are of small size.

The spraying station 34 of the sterilizing unit 26 is provided with at least one nozzle 43 located in the protective chamber 40. Each nozzle 43, during treatment, sprays a flow F of sterilizing vapour in the form of a jet of vapour, in this case towards the neck 16 of the preforms 12 to be sterilized, in such a way as to bring about the deposition, by condensation, of a substantially uniform film of condensate of sterilizing product, on at least the inner wall 15 of the preform, preferably on the inner wall 15 and the outside of the neck 16. In order so to do, the device delivers a flow of vapour which sweeps the outer wall of the neck.

Figure 3:
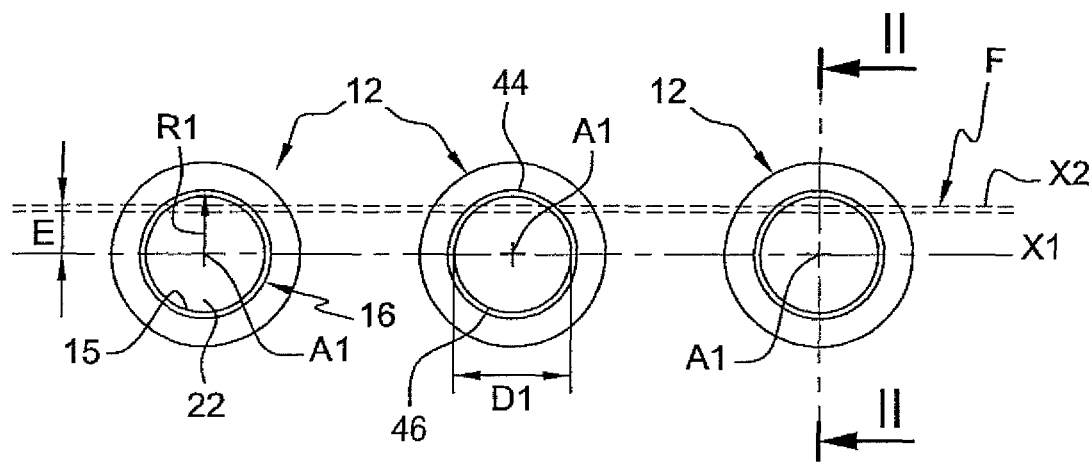
FIG. 3 is a view from above which shows a series of preforms at the spraying station of the sterilizing unit.

According to the embodiment shown here, especially in FIG. 3, the preforms 12 file into the spraying station 34 of the sterilizing unit 26 while being aligned, in a vertical position, in a longitudinal horizontal direction, termed running direction X1, with the neck 16 upwards.

The running direction X1 passes through the axes A1 of the preforms 12 being treated.

Advantageously, the mean spraying axis A2 of the nozzles 43 is generally parallel to the axis A1 of each preform 12 being treated, and the axis A2 is radially eccentric, relative to the axis A1 of the preform 12, by a specific offset value E.

Preferably, the mean spraying axis A2, which in this case is vertical, is eccentric along an inner radius R1 of the neck 16 which is perpendicular to the running direction X1.

Thus, the shape of each nozzle 43 makes it possible to spray downwards a flow F of sterilizing vapour generally in the form of a laminar flow, i.e. in the shape of a longitudinal vertical curtain. To this end, each nozzle 43 includes for example a slot or a generally circular hole for spraying the flow F.

The laminar flow F in this case extends generally in a curtain contained in a longitudinal vertical plane, termed spraying plane X2, which is radially offset, relative to the running direction X1, by a distance equal to the offset E.

Preferably, the offset value E ranges between a minimum value Emin substantially equal to 19% of the inside diameter D1 of the neck 16 of each preform 12, and a maximum value Emax substantially equal to 32% of the inside diameter D1.

According to an advantageous embodiment, the offset value E is selected to be fixed and substantially equal to 8 millimetres, such that it is suitable for models of preforms 12 having inside diameters D1 of between around 25 and 42 millimetres.

Owing to such an arrangement of the nozzles 43, the flow F of sterilizing vapour is substantially flush with a first sector 44 of the inner wall 15 of each preform 12, such that the flow F of sterilizing vapour sweeps said sector 44.

On arriving at the lower end 20 of the preform 12, the flow F of sterilizing vapour glides along the substantially hemispherical bottom of the preform 12 and rises along a second sector 46 of inner wall 15, diametrically opposed to the first 44.

Thus, the flow F of sterilizing vapour sweeps, overall, the whole of the inner wall 15 of each preform 12, by means of a laminar type of flow.

Such an arrangement makes it possible in particular to prevent the creation of a plug of over-pressure, in the bottom of the preforms 12, which would prevent the sterilizing product from reaching the bottom.

The nozzles 43 follow the trajectory of the preforms and diffuse vapour for a given time which corresponds to the deposition time.

The gaseous state of the flow F allows uniform diffusion over the whole surface area.

In particular, the spraying speed of the sterilizing vapour, at the outlet of the nozzle 43, is sufficiently low to permit the substantially laminar type of flow.

The preforms 12 passing through the plant 10, especially the sterilizing unit 26, are here oriented vertically with the neck 16 upwards, i.e. in the position termed "neck-up".

Thus, at the spraying station 34, the flow F of sterilizing vapour is vaporized onto each preform 12. The temperature T1 of the preforms is below the condensation temperature Tc of the sterilizing product, so that a film of condensate 48 of sterilizing product contained in the flow of sterilizing vapour is uniformly deposited, by condensation, at least on the inner wall 15, and preferably also on the outside of the neck 16 of the preform 12 to be sterilized.

At the outlet of the nozzle 43, the vapour containing the vaporized sterilizing product is at a given temperature substantially higher than the evaporation temperature Te of the sterilizing product, such that the sterilizing product condenses instantaneously on the preform 12.

In the case where a mixture of water and hydrogen peroxide ($H_2O_2$) is used, the exit temperature at the nozzle is advantageously above 106° C., preferably between 110° C. and 120° C.

When this vapour comes into contact with each preform 12, which is colder, the vaporized sterilizing product condenses so that the whole of the preform 12, in particular on the inner wall 15, is coated with a film of sterilizing product condensate 48.

The nozzle 43 is in this case produced in such a way that the substantially uniform film of condensate 48 is deposited mainly on the neck 16 and on the whole of the surface of the inner wall 15.

Advantageously, the deposition by condensation in the form of the uniform film of condensate 48 of sterile product makes it possible, compared with the prior art, substantially to eliminate any risk of occurrence of spots and "orange peel" appearance.

The spraying station 34 includes means 50 for forced extraction of the atmosphere from the chamber 40, through the extraction opening 40C. The aim of the means 50 is to recover the excess vaporized sterilizing product, i.e., that which is not deposited on the preforms, and also the hot air transporting the sterilizing product. The extraction means 50 thus make it possible substantially to avoid any emergence of vaporized sterilizing product through the entry/exit openings 40A, 40B for the preforms.

In order not to disturb the operation of the sterilizing unit, the extraction means 50 are regulated in such a way that the extraction rate is low enough for the flow of sterilizing vapour not to be noticeably deflected.

The inventors observed that only 15% to 25% of the flow rate of vaporized sterilizing product contained in the flow of sterilizing vapour sprayed by the nozzles 43 was deposited on the preforms 12 to form the film of condensate 48. Thus, satisfactory regulation of the rate of extraction through the extraction opening 40C is obtained by regulating the rate to be equal to the sum:

of an escape flow rate penetrating through the entry/exit openings 40A, 40B, of 75% to 85% of the spraying flow rate of the vaporized sterilizing product, of the hot air flow rate (100%−P).

In other words, the extraction rate is regulated to be equal to the sum of, on the one hand, the escape flow rate penetrating through the entry/exit openings 40A, 40B and, on the other hand, the flow rate of the flow of sterilizing vapour less 15% to 25% of the flow rate of sterilizing product sprayed in the flow of sterilizing vapour.

In practice, this satisfactory regulation is obtained empirically, by observation of test preforms emerging from the spraying station 34, to check that an adequate film of condensate 48 is in fact present and that there is no appearance of condensate on the inner walls of the enclosures 40.

The heating station 38 is located outside the protective chamber 40, downstream of this latter. The conveying means 25, before the entry into the heating station 38, proceed to invert the preforms 12, which then file through "neck-down". In fact, because of physical phenomena and effects due to ventilation, the flow of heat in the ovens is directed from bottom to top. The neck is the part definitively moulded in the blow moulding process and should not undergo either deformation or overheating. The primary risk linked to overheating is the bursting of the neck during the moulding of the bottle. The neck in the low position (preforms "neck-down") is therefore positioned so as to avoid overheating and is also protected by cooled ramps (not shown) from the infra-red radiation.

The heating station 38 includes at least one oven 42 intended to heat, by radiation, the preforms 12 provided with the film of condensate 48, to bring them to a temperature T at or above a temperature Ta for activation of the sterilizing product, such as to sterilize at least the inner wall 15 of the preforms 12, and preferably also the neck 16. In order not to overload FIG. 1, the oven 42 is arranged above the preforms 12, opposite their base 20, whereas in reality the heating means constituting the oven are arranged on each side of the transport path of the preforms in the oven.

The heating station 38, in addition to the function of activation of the film of sterilizing product, has the function of preparing the preforms 12 for moulding.

Thus, the preforms 12 are in fact heated to a moulding temperature Tm which, depending on the type of preform, varies between 95° C. and 135° C. This temperature Tm is in this case above the activation temperature Ta of the sterilizing product and the evaporation temperature Te, permitting the elimination of the sterilizing product by evaporation, without requiring supplementary means.

In fact, the activation temperature Ta of hydrogen peroxide ($H_2O_2$) is around 70° C., i.e. in this case a temperature below the moulding temperature Tm.

In general, the oven 42 is configured to bring the preforms 12, provided with the film of sterilizing product, to the highest of the three temperatures Tm, Ta and Te.

The oven 42 is preferably equipped with aeration apertures (not shown) to permit the passage of blown air, in order to facilitate homogeneous heating throughout the thickness of the preform 12 without overheating the surface layer of material.

In fact, the blown air makes it possible to evacuate the convection heat produced by the heating means in order to facilitate the penetration of the radiation which they produce into the thickness of the material forming the preform 12.

For more details concerning such preform heating ovens 42, reference will be made for example to the following documents: EP-A-0 620 099 or EP-A-0 564 354.

Preferably, the oven 42 includes protection means, especially for limiting the corrosion of the portions or parts exposed to the sterile product which evaporates from the preforms 12.

The transport means 25 advantageously include means 52 for setting the preforms 12 in rotation on themselves during their circulation in the oven 42 so as to ensure thorough heating of the preform 12, i.e. both of the lower end 20 forming the bottom, and of the cylindrical body 18. The document WO-A-00/48819, to which reference will be made for more details, describes an example of such means.

The transport means 25 further include, at the heating station 38, at least one means, such as an inner core 54, also known as a spinner pivot, which penetrates axially inside the neck 16 of each preform 12, obstructing all or part of the inner opening 22 defined by the neck 16 so as to increase the degree of sterilization by increasing the length of time for which the inner wall 15 of the preform 12 is exposed to the sterilizing product.

As will have been understood, at the outlet of the oven 42 preforms 12 are obtained which are mainly sterile inside and should advantageously remain sterile until the final stoppering operation.

The forming unit 28, in addition to the heating station 38, comprises a moulding station 55. The moulding station 55 includes a blow moulding device 56 which subjects each preform 12 to an internal over-pressure such that it assumes the shape of the impression of a mould 58, thereby producing a sterile bottle 14.

The moulding station 34 may also include elongation means (not shown) which stretch the preform 12 towards the bottom of the mould 58 during the moulding operation.

A description will now be given of the operation of the sterilizing unit 26.

In order to sterilize especially the inner wall 15 of the preform 12, the following steps are performed consecutively:

checking that the preform 12 is at a temperature T1 below the condensation temperature Tc of the sterilizing product;

bringing the preform into the chamber 40, spraying a flow F of sterilizing vapour, containing a vaporized sterilizing product, in the form of a jet of vapour, towards the neck 16 of the preform 12 in such a way as to bring about the deposition, by condensation, of a substantially uniform film of condensate 48 of sterilizing product at least on the inner wall 15 of the preform 12 to be sterilized; and removing the preform provided with the film of condensate 48 from the chamber 40 and heating, by radiation, the preform 12 thus treated in order to bring the preform 12 to a temperature T2 at or above the activation temperature Ta of the sterilizing product, so as to sterilize at least the inner wall 15 of the preform 12.

The temperature T2 is therefore higher than the evaporation temperature Te of the sterilizing product, so as to bring about its elimination by evaporation simultaneously with its thermal activation by radiation.

The condensation temperature Tc of hydrogen peroxide is above approximately 35° C. Thus, when the preform 12 is at a temperature substantially equal to the ambient temperature of the plant 10, for example between 7° C. and 35° C., good condensation of the vaporized sterilizing product is easily obtained.

Moreover, verification of the temperature is then simplified. In fact, it is not necessary to modify the temperature of the preform 12 by heating or cooling, in order to obtain the condensation of the sterilizing product on the inner wall 15 of the preform.

According to an alternative embodiment (not shown) of the plant 10, a sterile containment enclosure may be provided to make it possible to control and preserve the sterility of the sterilized preforms 12 and of the bottles 14 between the different units or different stations of the plant.

By means of a plant 10 according to FIG. 1, a logarithmic reduction of the number of germs of the order of 3D, or even Log 3 equivalent to 1000 units (103) is obtained.

In a known manner, the quantity of germs is enumerated for example by counting after washing, filtration and culturing operations.

It will be noted that the plant 10 has been shown with treatment units such as the sterilizing unit 26, the forming unit 28, the filling unit 30, and the stoppering unit 32. These units are aligned, by way of illustration, but the units may be arranged in a different configuration, especially with rotating transport means such as turntables.

The invention claimed is:

1. A method for sterilizing a line of preforms made of plastics material that are intended to be moulded, especially by blow moulding, including at least the following steps:

spraying a flow of sterilizing vapor, including a vaporized sterilizing product, towards the preforms to be sterilized, so as to cover at least an inner wall of the preforms to be sterilized with the product, and heating, by radiation, the preforms covered with sterilizing product to bring them to a temperature at or above an activation temperature for the product, wherein:

the spraying of the flow of sterilizing vapor is carried out in a protective chamber, heating is carried out outside the protective chamber, and the flow of sterilizing vapor is in the form of a jet of vapor vaporized onto the preforms, in such a way as to bring about the deposition, by condensation, of a substantially uniform film of condensate of sterilizing product on at least the inner wall of the preforms to be sterilized, wherein the method includes a step of extraction of the atmosphere from the protective chamber, in order substantially to avoid any emergence of the vaporized sterilizing product through entry/exit openings for the preforms, provided in the protective chamber, and wherein the spraying step is carried out while the preforms are being maintained at a temperature between 7 and 35° C.

2. A sterilizing method according to claim 1, characterized in that extraction is carried out at an extraction rate low enough for the flow of sterilizing product not to be noticeably deflected.

3. A method according to claim 2, characterized in that the temperature to which the preforms are brought is substantially equal to a moulding temperature for blow moulding of the preforms which is respectively above the activation temperature and an evaporation temperature of the sterilizing product.

4. A sterilizing method according to claim 2, characterized in that the protective chamber is pierced only by entry/exit openings for the preform and by an extraction opening.

5. A method according to claim 4, characterized in that the temperature to which the preforms are brought is substantially equal to a moulding temperature for blow moulding of the preforms which is respectively above the activation temperature and an evaporation temperature of the sterilizing product.

6. A sterilizing method according to claim 4, characterized in that the rate of extraction through the extraction opening is regulated to be equal to the sum, on the one hand, of an escape flow rate penetrating through the entry/exit openings and, on the other hand, of the flow rate of the flow of sterilizing vapor less 15% to 25% of the flow rate of sterilizing product sprayed in the flow of sterilizing vapor.

7. A method according to claim 6, characterized in that the temperature to which the preforms are brought is substantially equal to a moulding temperature for blow moulding of the preforms which is respectively above the activation temperature and an evaporation temperature of the sterilizing product.

8. A method according to claim 1, characterized in that the temperature to which the preforms are brought is substantially equal to a moulding temperature for blow moulding of the preforms which is respectively above the activation temperature and an evaporation temperature of the sterilizing product.

9. A method for sterilizing a line of preforms made of plastics material that are intended to be moulded, especially by blow moulding, including at least the following steps:

spraying a flow of sterilizing vapor, including a vaporized sterilizing product, towards the preforms to be sterilized, so as to cover at least an inner wall of the preforms to be sterilized with the product, and heating, by radiation, the preforms covered with sterilizing product to bring them to a temperature at or above an activation temperature for the product, wherein:

the spraying of the flow of sterilizing vapor is carried out in a protective chamber, heating is carried out outside the protective chamber, and the flow of sterilizing vapor is in the form of a jet of vapor vaporized onto the preforms, in such a way as to bring about the deposition, by condensation, of a substantially uniform film of condensate of sterilizing product on at least the inner wall of the preforms to be sterilized, wherein the method includes a step of extraction of the atmosphere from the protective chamber, in order substantially to avoid any emergence of the vaporized sterilizing product through entry/exit openings for the preforms, provided in the protective chamber, wherein, during the spraying step:

the preforms are aligned in a vertical position, in a longitudinal horizontal direction, termed running direction, with a neck of the preforms upwards; and said spraying is performed through nozzles, said nozzles defining a mean spraying axis which is generally parallel to a longitudinal axis of each preform being treated, said mean spraying axis being radially eccentric, relative to the axes of the preforms, by a specific offset value, whereby the flow of vapor extends in a curtain, and the preforms file through said curtain.

10. A sterilizing method according to claim 9, characterized in that extraction is carried out at an extraction rate low enough for the flow of sterilizing product not to be noticeably deflected.

11. A method according to claim 10, characterized in that the temperature to which the preforms are brought is substantially equal to a moulding temperature for blow moulding of the preforms which is respectively above the activation temperature and an evaporation temperature of the sterilizing product.

12. A sterilizing method according to claim 10, characterized in that the protective chamber is pierced only by entry/exit openings for the preform and by an extraction opening.

13. A method according to claim 12, characterized in that the temperature to which the preforms are brought is substantially equal to a moulding temperature for blow moulding of the preforms which is respectively above the activation temperature and an evaporation temperature of the sterilizing product.

14. A sterilizing method according to claim 12, characterized in that the rate of extraction through the extraction opening is regulated to be equal to the sum, on the one hand, of an escape flow rate penetrating through the entry/exit openings and, on the other hand, of the flow rate of the flow of sterilizing vapor less 15% to 25% of the flow rate of sterilizing product sprayed in the flow of sterilizing vapor.

15. A method according to claim 14, characterized in that the temperature to which the preforms are brought is substantially equal to a moulding temperature for blow moulding of the preforms which is respectively above the activation temperature and an evaporation temperature of the sterilizing product.

16. A method according to claim 9, characterized in that the temperature to which the preforms are brought is substantially equal to a moulding temperature for blow moulding of the preforms which is respectively above the activation temperature and an evaporation temperature of the sterilizing product.

17. A method according to claim 9, wherein each preform has a neck having an inside diameter, and said offset value is in the range 19%-32% of said inside diameter.

18. A method according to claim 9, wherein the spraying step is carried out while the preforms are being maintained at a temperature between 7 and 35° C.

* * * * *